(12) United States Patent
Young et al.

(10) Patent No.: US 7,875,182 B2
(45) Date of Patent: Jan. 25, 2011

(54) SIZE-SELECTIVE HEMOPERFUSION POLYMERIC ADSORBENTS

(75) Inventors: Wei-Tai Young, Hillsborough, NJ (US); Robert L. Albright, Southampton, PA (US); Thomas D. Golobish, Princeton, NJ (US)

(73) Assignee: Cytosorbents, Inc., Monmouth Junction, NJ (US)

( * ) Notice: Subject to any disclaimer, the term of this patent is extended or adjusted under 35 U.S.C. 154(b) by 0 days.

(21) Appl. No.: 11/601,931

(22) Filed: Nov. 20, 2006

(65) Prior Publication Data

US 2008/0119576 A1 May 22, 2008

(51) Int. Cl.
*B01D 11/00* (2006.01)
*C08J 9/00* (2006.01)
*C08J 9/26* (2006.01)
*C08J 9/32* (2006.01)
*B29C 44/34* (2006.01)
*A23J 1/00* (2006.01)

(52) U.S. Cl. .................. 210/645; 424/529; 424/634; 424/644; 521/50; 521/61; 521/76; 521/134; 521/142; 530/415

(58) Field of Classification Search ............ 521/50, 521/61, 76, 134, 142; 210/645; 424/529, 424/634, 644; 530/415
See application file for complete search history.

(56) References Cited

U.S. PATENT DOCUMENTS

| | | |
|---|---|---|
| 3,794,584 A | 2/1974 | Kunin |
| 4,048,064 A | 9/1977 | Clark, III |
| 4,171,283 A | 10/1979 | Nakashima et al. |
| 4,224,415 A | 9/1980 | Meitzner et al. |
| 4,246,351 A | 1/1981 | Miyake et al. |
| 4,297,220 A | 10/1981 | Meitzner et al. |
| 4,300,551 A | 11/1981 | Kinney |
| 5,051,185 A | 9/1991 | Watanabe et al. |
| 5,149,425 A | 9/1992 | Mazid |
| 5,545,131 A | 8/1996 | Davankov et al. |
| 5,773,384 A | 6/1998 | Davankov et al. |
| 5,904,663 A | 5/1999 | Braverman et al. |
| 6,087,300 A | 7/2000 | Davankov et al. |
| 6,114,466 A | 9/2000 | Davankov et al. |
| 6,127,311 A | 10/2000 | Davankov et al. |
| 6,132,610 A | 10/2000 | Hirai et al. |
| 6,133,393 A | 10/2000 | Davankov et al. |
| 6,136,424 A | 10/2000 | Davankov et al. |
| 6,153,707 A | 11/2000 | Davankov et al. |
| 6,156,851 A | 12/2000 | Davankov et al. |
| 6,159,377 A | 12/2000 | Davankov et al. |
| 6,238,795 B1 | 5/2001 | Strom et al. |
| 6,303,702 B1 | 10/2001 | Davankov et al. |
| 6,315,907 B1 | 11/2001 | Hirai et al. |
| 6,325,939 B2 | 12/2001 | Strom et al. |
| 6,338,801 B2 | 1/2002 | Strom et al. |
| 6,387,362 B1 | 5/2002 | Hirai et al. |
| 6,408,894 B1 | 6/2002 | Davankov et al. |
| 6,416,487 B1 | 7/2002 | Braverman et al. |
| 6,419,830 B2 | 7/2002 | Strom et al. |
| 6,497,675 B1 | 12/2002 | Davankov et al. |
| 6,527,735 B1 | 3/2003 | Davankov et al. |
| 6,531,523 B1 | 3/2003 | Davankov et al. |
| 6,551,700 B2 | 4/2003 | Giebelhausen |
| 6,559,290 B1 * | 5/2003 | Nakatani et al. ............ 530/415 |
| 6,569,112 B2 | 5/2003 | Strahilevitz |
| 6,582,811 B1 | 6/2003 | Davankov et al. |
| 6,600,014 B2 | 7/2003 | Ogino et al. |
| 6,676,622 B2 | 1/2004 | Strahilevitz |

* cited by examiner

*Primary Examiner*—Mark Eashoo
*Assistant Examiner*—Melissa Rioja
(74) *Attorney, Agent, or Firm*—Dan M. De La Rosa

(57) ABSTRACT

Size-selective hemocompatible porous polymeric adsorbents are provided with a pore structure capable of excluding molecules larger than 50,000 Daltons, but with a pore system that allows good ingress and egress of molecules smaller than 35,000 Daltons. The pore system in these porous polymeric adsorbents is controlled by the method of synthesis so that 98% of the total pore volume is located in pores smaller than 300 Angstroms (Å) in diameter with a working pore size range within 100 to 300 Å in diameter. The porous polymeric adsorbents of this invention are very selective for extracting midsize proteins, such as cytokines and $\beta_2$-microglobulin, from blood and other physiologic fluids while keeping the components required for good health such as cells, platelets, albumin, hemoglobin, fibrinogen, and other serum proteins intact.

17 Claims, 1 Drawing Sheet

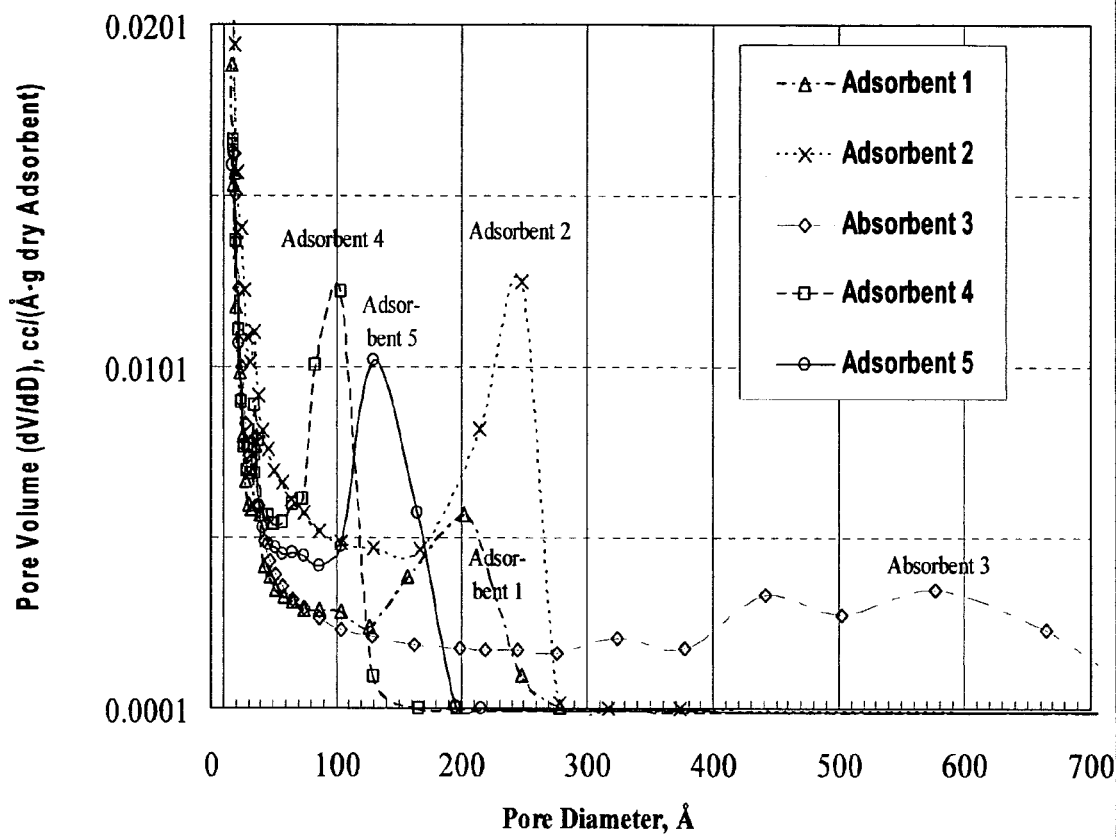

SIZE-SELECTIVE HEMOPERFUSION POLYMERIC ADSORBENTS

BACKGROUND OF INVENTION

1. Field of Invention

The size-selective porous polymeric adsorbents of this invention are biocompatible and hemocompatible and are designed to function in direct contact with body fluids. These adsorbents are useful in conjunction with hemodialysis for extracting and controlling the blood level of $\beta_2$-microglobulin without significantly perturbing the levels of albumin, immunoglobulins, leukocytes, erythrocytes, and platelets. These polymeric adsorbents are also very effective in extracting cytokines from the blood of patients with sepsis while keeping the physiologically required components of blood at clinically acceptable levels. These adsorbents are also useful for purification of blood plasma by their ability to remove selectively small to midsize protein toxins without disturbing the level of the other plasma components.

2. Description of Related Art

Techniques of extracorporeal blood purification are important in many medical treatments including hemodialysis, hemofiltration, hemoperfusion, plasma perfusion and combinations of these methods. Hemodialysis and hemofiltration involve passing whole blood through hollow fibers to remove excess water and compounds of small molecular size but are unable to remove protein toxins such as beta-2-microglobulin (B2M) and the cytokines. Hemoperfusion is passing whole blood over an adsorbent to remove contaminants from the blood. Plasma perfusion is passing blood plasma through an adsorbent. In hemoperfusion, the treated whole blood returns to the patient's blood circulation system.

In addition to the common requirements such as hemocompatibility and sterility for medical devices, an ideal adsorbent for hemoperfusion and plasma perfusion should have an adsorption capacity and selectivity adequate for adsorbing toxins to the exclusion of useful components in order to be beneficial to the patient.

Conventional adsorbing materials include activated carbon, silicates, diatomite and synthetic porous resins. Activated carbon has been reported in extracorporeal adsorption for treating schizophrenia (Kinney, U.S. Pat. No. 4,300,551; 1981). Various synthetic polymeric adsorbents have been disclosed for removing toxic shock syndrome toxin-1, bradykinin and endotoxin from blood (Hirai, et al. U.S. Pat. No. 6,315,907; 2001; U.S. Pat. No. 6,387,362; 2002, and U.S. Pat. No. 6,132,610; 2000), and for removing poisons and/or drugs from the blood of animals (Kunin, et al., U.S. Pat. No. 3,794,584; 1974). Adsorption by the above adsorbents is generally rather nonselective and, therefore, is limited to short term treatments.

Most commercial porous resins are synthesized either by macroreticular synthesis (Meitzner, et al., U.S. Pat. No. 4,224,415; 1980), such as Amberlite XAD-4® and Amberlite XAD-16® by Rohm and Haas Company or by hypercrosslinking synthesis [Davankov, et al. J. Polymer Science, Symposium No. 47, 95-101 (1974)], used to make the Hpersol-Macronet® resins by Purolite Corp. Many conventional polymeric adsorbents have a large pore surface and adsorption capacity but a lack of selectivity due to the broad distribution of pore sizes. Others are produced to adsorb small organic molecules or are not hemocompatible and therefore are not suitable for selective adsorption of midsize proteins directly from body fluids.

In order to enhance the hemocompatibility, many techniques involve coating the hydrophobic adsorbent with hydrophilic materials such as polyacrylamide and poly(hydroxyethylmethacrylate) (Clark, U.S. Pat. No. 4,048,064; 1977; Nakashima, et al., U.S. Pat. No. 4,171,283; 1979). A copolymer coating of 2-hydroxyethyl methacrylate with diethylaminoethyl methacrylate is reported by Watanabe, et al. (U.S. Pat. No. 5,051,185; 1991). Davankov, et al. (U.S. Pat. No. 6,114,466; 2000) disclosed a method of grafting to the external surface of porous polymeric beads hydrophilic monomers including 2-hydroxyethyl methacrylate, N-vinylpyrrolidinone, N-vinylcaprolactam and acrylamide. Recently, Albright (U.S. Pat. No. 6,884,829 B2; 2005) disclosed the use of surface active dispersants [including polyvinyl alcohol, poly(dimethylaminoethyl methacrylate), poly (vinylpyrrolidinone), and hydroxyethylcellulose] during macroreticular synthesis to yield a hemocompatible surface on porous beads in a one step synthesis.

The internal pore structure (distribution of pore diameters, pore volume, and pore surface) of the adsorbent is very important to adsorption selectivity. A cartridge containing a packed bed of adsorbent with effective pore diameters ranging from 2 Å to 60 Å (Angstrom) was disclosed for hemoperfusion by Clark (U.S. Pat. No. 4,048,064; 1977). This pore size range was primarily specified for detoxification and preventing adsorption of anticoagulants, platelets and leukocytes from the blood but is inadequate for adsorbing midsize proteins such as cytochrome-c and beta-2-microglobulin. Similarly, coating inorganic adsorbents, such as silicate and diatomite, with a membrane film having pore sizes greater than 20 Å was disclosed by Mazid (U.S. Pat. No. 5,149,425; 1992) for preparing hemoperfusion adsorbents. More recently, Giebelhausen (U.S. Pat. No. 551,700; 2003) disclosed a spherical adsorbent with pronounced microstructure with 0-40 Å pore diameters and an overall micropore volume of at least 0.6 cm³/g for adsorption of chemical warfare agents, toxic gases and vapors, and refrigerating agents. The above pore structures are too small for adsorption of midsize proteins from physiologic fluids.

An adsorbent with a broad distribution of pore sizes (40~9,000 Å diameter) was disclosed for adsorbing proteins, enzymes, antigens, and antibodies by Miyake et al. (U.S. Pat. No. 4,246,351; 1981). The adsorbent sorbs both the toxins as well as the beneficial proteins such as albumin from the blood due to its broad pore size distribution. Immobilizing antibodies and IgG-binding proteins onto porous polymeric adsorbents were described to enhance selectivity of adsorbents having broad pore size distributions for lowering low density lipoproteins, for treating atherosclerosis, for adsorbing rheumatoid arthritis factor (Strahilevitz, U.S. Pat. No. 6,676,622; 2004), and for removing hepatitis C virus from blood (Ogino et al. U.S. Pat. No. 6,600,014; 2003). The antibodies or proteins bound to adsorbents, however, could greatly increase the side effects for a hemoperfusion or a plasma perfusion device and could greatly increase the difficulty for maintaining sterility of the devices.

Removal of beta-2-microglobulin by direct hemoperfusion was beneficial to renal patients (Kazama, "Nephrol. Dial. Transplant", 2001, 16:31-35). An adsorbent with an enhanced portion of pores in a diameter range between 10 and 100 Å was described by Braverman et al. (U.S. Pat. No. 5,904,663; 1999) for removing beta-2-microglobulin from blood and by Davankov et al (U.S. Pat. No. 6,527,735; 2003) for removing toxins in the molecular weight range of 300-30,000 daltons from a physiologic fluid. Strom, et al. (U.S. Pat. No. 6,338,801; 2002) described a synthesis method for polymer resins with pore sizes in the range from 20 Å to 500 Å intended for adsorbing beta-2-microglobulin. The in-vitro study by the present inventors shows that the pore structures proposed by Davankov and Strom, however, are inadequate for a selective adsorption of midsize proteins such as beta-2-microglobulin and cytochrome-c in the presence of serum albumin.

In contrast to prior disclosures, the porous polymeric adsorbents specified in the present invention demonstrate a high selectivity for adsorbing small and midsize proteins to the exclusion of the large proteins with molecular weights greater than 50,000 daltons. More significantly, the present invention discloses adsorbents for hemoperfusion suitable for long term clinical treatment, since the healthy components such as albumin, red blood cells, platelets and white blood cells are maintained at clinically acceptable levels.

SUMMARY OF INVENTION

In one embodiment, the present invention relates to a porous polymer for sorbing small to midsize protein molecules and excluding sorption of large blood proteins, the polymer comprising a plurality of pores. The pores sorb small to midsize protein molecules equal to or less than 50,000 Daltons. In another embodiment, the polymer is biocompatible and/or hemocompatible.

In yet another embodiment, the polymer comprises a plurality of pores with diameters from about 75 Angstrom to about 300 Angstrom. In another embodiment, the polymer can have a plurality of pores within the above range. In another further embodiment, the polymer has its working pores within the above mentioned range and can also have non-working pores below the 75 Angstrom range. In another embodiment, the polymer has no more than 2.0 volume % of its total pore volume in pores with diameters greater than 300 Angstroms. For purposes of this invention, the term "large blood proteins" is defined as any blood protein greater than 50,000 Daltons in size and the term "blood protein molecules" relates to small to midsize blood proteins equal to or less than 50,000 Daltons.

In still yet another embodiment, the geometry of the polymer is a spherical bead. In a further embodiment, the polymer has a pore volume greater than 98.0% in pores smaller than 300 Angstroms diameter.

In another further embodiment, the polymer is used in direct contact with whole blood to adsorb protein molecules such as $\beta_2$-microglobulin but excluding the sorption of larger blood proteins, said large blood proteins being selected from a group consisting essentially of hemoglobin, albumin, immunoglobulins, fibrinogen, serum proteins larger than 50,000 Daltons and mixtures thereof. In yet another further embodiment, the polymer has an internal surface selectivity for adsorbing proteins smaller than 50,000 Daltons, having little to no selectivity for adsorbing vitamins, glucose, electrolytes, fats, and other hydrophilic small molecular nutrients carried by the blood.

In still a further embodiment, the polymer is made porous using macroreticular synthesis or macronet synthesis. In still yet a further embodiment, the polymer is made using suspension polymerization.

In another embodiment, the polymer is constructed from aromatic monomers of styrene and ethylvinylbenzene with crosslinking provided by divinylbenzene, trivinylcyclohexane, trivinylbenzene, divinylnaphthalene, divinylsulfone, trimethylolpropane triacrylate, trimethylolpropane trimethacrylate and mixtures thereof.

In yet another embodiment, the stabilizing agent for the droplet suspension polymerization is selected from a group consisting essentially of hemocompatibilizing polymers, said polymers being poly(N-vinylpyrrolidinone), poly(hydroxyethyl acrylate), poly(hydroxyethyl methacrylate), hydroxylethyl cellulose, hydroxypropyl cellulose, salts of poly(acrylic acid), salts of poly(methacrylic acid), poly(dimethylaminoethyl acrylate), poly(dimethylaminoethyl methacrylate), poly(diethylaminoethyl acrylate), poly(diethylaminoethyl methacrylate), poly(vinyl alcohol) and mixtures thereof.

In still another embodiment, the polymer is made hemocompatible by exterior coatings of poly(N-vinylpyrrolidinone), poly(hydroxyethyl acrylate), poly(hydroxyethyl methacrylate), hydroxyethyl cellulose, hydroxypropyl cellulose, salts of poly(acrylic acid), salts of poly(methacrylic acid), poly(dimethylaminoethyl methacrylate), poly(dimethylaminoethyl acrylate), poly(diethylaminoethyl acrylate), poly(diethylaminoethyl methacrylate), poly(vinyl alcohol) and mixtures thereof.

In yet another embodiment, the polymer is made hemocompatible by surface grafting of the hemocompatible exterior coatings concomitantly with formation of the porous polymer beads. In still yet another embodiment, the polymer is made hemocompatible by surface grafting of the hemocompatible exterior coatings onto the preformed porous polymeric beads.

In a further embodiment, the present invention relates to a polymer absorbent for excluding albumin from sorption. The polymer comprises pores with diameters from about 75 Angstrom to about 300 Angstrom.

In another further embodiment, the present invention provides a hemocompatible polymer comprising a working pore range. The working pore range has pore diameters from about 75 Angstrom to about 300 Angstrom and the polymer is designed to adsorb blood protein molecules.

In another embodiment, the present invention relates to a size selective polymer for sorbing small to midsize blood borne proteins and excluding the sorption of large blood borne proteins; the polymer comprises a plurality of pores, and the pores have diameters from about 75 Angstrom to about 300 Angstrom. The polymer is used in direct contact with whole blood to adsorb cytokines and $\beta_2$-microglobulin but excludes the adsorption of large blood borne proteins, and the large blood borne proteins are selected from a group consisting essentially of hemoglobin, albumin, immunoglobulins, fibrinogen, serum proteins larger than 50,000 Daltons and mixtures thereof. For purposes of this invention, the term "blood borne proteins" includes enzymes, hormones and regulatory proteins such as cytokines and chemokines.

The present invention discloses size-selective, biocompatible, and hemocompatible porous polymeric adsorbents whose pore structures are designed for efficacy in hemoperfusion. For efficacy in hemoperfusion, the adsorbents must sorb proteins selectively over the other small molecular species and the hydrophilic molecules present in blood. The protein sorption must also be restricted to molecular sizes smaller than 50,000 daltons so that the important proteins required for health homeostasis—albumin, immunoglobulins, fibrinogen—remain in the blood during the hemoperfusion treatment.

The porous polymeric adsorbents of this invention have a hemocompatible exterior surface coating and an internal pore system with an aromatic pore surface for protein selectivity and a major pore volume falling within the pore diameter range of 100 to 300 Å with essentially no pores larger than 300 Å in diameter. The pore volume in pores larger than 300 Å is 2.0% or less of the total pore volume. These porous polymeric adsorbents exclude entrance into the pore system of protein molecules larger than 50,000 Daltons but provide good mass transport into the pore system for the protein molecules with sizes smaller than 35,000 Daltons.

The porous polymers of this invention are constructed from aromatic monomers of styrene and ethylvinylbenzene with crosslinking provided by one of the following or mixtures of the following of divinylbenzene, trivinylcyclohexane, trimethylolpropane triacrylate and trimethylolpropane trimethacrylate. Other crosslinking agents that may be used to construct the porous polymeric adsorbents of this invention are divinylnaphthalene, trivinylbenzene and divinylsulfone and mixtures thereof.

The porous polymers of this invention are made by suspension polymerization in a formulated aqueous phase with free radical initiation in the presence of aqueous phase dispersants that are selected to provide a biocompatible and a hemocompatible exterior surface to the formed polymer beads. The beads are made porous by the macroreticular synthesis with an appropriately selected porogen (precipitant) and an appropriate time-temperature profile for the polymerization in order to develop the proper pore structure.

Porous beads are also made with small pore sizes by the hypercrosslinking methodology which is also known as macronetting or the macronet synthesis. In this methodology, a lightly crosslinked gel polymer—crosslinking usually less than two (2) wt. %—is swelled in a good difunctional swelling agent for the polymeric matrix. In the swollen state, the polymeric matrix is crosslinked by a catalyzed reaction. The catalyzed reaction is most often a Friedel-Crafts reaction catalyzed by a Lewis-acid catalyst. The resulting product is a macroporous polymer which is a crosslinked polymer having a permanent pore structure in a dry, non-swollen state.

For the purposes of this invention, the term "biocompatible" is defined as a condition of compatibility with physiologic fluids without producing unacceptable clinical changes within the physiologic fluids. The term "hemocompatible" is defined as a condition whereby a material when placed in contact with whole blood or blood plasma results in clinically acceptable physiologic changes.

The biocompatible and hemocompatible exterior surface coatings on the polymer beads are covalently bound to the bead surface by free-radical grafting. The free-radical grafting occurs during the transformation of the monomer droplets into polymer beads. The dispersant coating and stabilizing the monomer droplets becomes covalently bound to the droplet surface as the monomers within the droplets polymerize and are converted into polymer. Biocompatible and hemocompatible exterior surface coatings can be covalently grafted onto the preformed polymer beads if the dispersant used in the suspension polymerization is not one that imparts biocompatibility or hemocompatibility. Grafting of biocompatible and hemocompatible coatings onto preformed polymer beads is carried out by activating free-radical initiators in the presence of either the monomers or low molecular weight oligomers of the polymers that impart biocompatibility or hemocompatibility to the surface coating.

Biocompatible and hemocompatible exterior surface coatings on polymer beads are provided by a group of polymers consisting of poly(N-vinylpyrrolidinone), poly(hydroxyethyl methacrylate), poly(hydroxyethyl acrylate), hydroxyethyl cellulose, hydroxypropyl cellulose, salts of poly(acrylic acid), salts of poly(methacrylic acid), poly(dimethylaminoethyl methacrylate), poly(dimethylaminoethyl acrylate), poly(diethylaminoethyl acrylate), poly(diethylaminoethyl methacrylate), and poly(vinyl alcohol).

The hemoperfusion and perfusion devices consist of a packed bead bed of the size-selective porous polymer beads in a flow-through container fitted with a retainer screen at both the exit end and the entrance end to keep the bead bed within the container. The hemoperfusion and perfusion operations are performed by passing the whole blood, blood plasma or physiologic fluid through the packed bead bed. During the perfusion through the bead bed, the protein molecules smaller than 35,000 Daltons are extracted by adsorption while the remainder of the fluid components pass through essentially unchanged in concentration.

For the purposes of this invention, the term "perfusion" is defined as passing a physiologic fluid by way of a suitable extracorporeal circuit through a device containing the porous polymeric adsorbent to remove toxins and proteins from the fluid. The term "hemoperfusion" is a special case of perfusion where the physiologic fluid is blood. The term "dispersant" or "dispersing agent" is defined as a substance that imparts a stabilizing effect upon a finely divided array of immiscible liquid droplets suspended in a fluidizing medium. The term "macroreticular synthesis" is defined as a polymerization of monomers into polymer in the presence of an inert precipitant which forces the growing polymer molecules out of the monomer liquid at a certain molecular size dictated by the phase equilibria to give solid nanosized microgel particles of spherical or almost spherical symmetry packed together to give a bead with physical pores of an open cell structure [U.S. Pat. No. 4,297,220, Meitzner and Oline, Oct. 27, 1981; R. L. Albright, Reactive Polymers, 4, 155-174(1986)]. For purposes of this invention, the term "sorb" is defined as "taking up and binding by absorption and adsorption".

BRIEF DESCRIPTION OF THE DRAWINGS

The accompanying drawings are included to provide a further understanding of the present invention. These drawings are incorporated in and constitute a part of this specification, illustrate one or more embodiments of the present invention and together with the description, serve to explain the principles of the present invention.

FIG. 1 is a graph of Table 2 showing a plot of pore volume v pore diameter (dV/dD vs. D) for Various Adsorbents Measured by Nitrogen Desorption Isotherm.

Among those benefits and improvements that have been disclosed, other objects and advantages of this invention will become apparent from the following description taken in conjunction with the accompanying drawings. The drawings constitute a part of this specification and include exemplary embodiments of the present invention and illustrate various objects and features thereof.

DETAILED DESCRIPTION OF THE INVENTION

As required, detailed embodiments of the present invention are disclosed herein; it is to be understood that the disclosed embodiments are merely exemplary of the invention that may be embodied in various forms. Therefore, specific structural and functional details disclosed herein are not to be interpreted as limits, but merely as a basis for teaching one skilled in the art to employ the present invention. The specific examples below will enable the invention to be better understood. However, they are given merely by way of guidance and do not imply any limitation.

Five porous polymeric adsorbents are characterized for their pore structures and are assessed for their competitive adsorption of cytochrome-c (11,685 Daltons in size) over serum albumin (66,462 Daltons in size). The adsorbent syntheses are described in Example 1; the pore structure characterization is given in Example 2; the competitive dynamic adsorption procedure and results are provided in Example 3; and the competitive efficacy for pick up the smaller cyctochrome-c protein over the larger albumin molecule is discussed under Example 4.

EXAMPLE 1

Adsorbent Syntheses

The synthesis process consists of (1) preparing the aqueous phase, (2) preparing the organic phase, (3) carrying out the suspension polymerization, and (4) purifying the resulting porous polymeric adsorbent product. The aqueous phase compositions are the same for all the polymerizations. Table 1A lists the percentage composition of the aqueous phase and Table 1B gives the material charges typical for a five (5) liter-reactor polymerization run.

TABLE 1A

Aqueous Phase Composition

| | Wt. % |
|---|---|
| Ultrapure Water | 97.787 |
| Dispersing Agent: Polyvinylalcohol | 0.290 |
| Monosodium Phosphate | 0.300 |
| Disodium Phosphate | 1.000 |
| Trisodium Phosphate | 0.620 |
| Sodium Nitrite | 0.003 |

TABLE 1B

Material Charges for a Typical Five (5) Liter-Reactor Polymerization Run

| | |
|---|---|
| Volume of Aqueous Phase | 1750.00 ml |
| Density of Aqueous Phase | 1.035 g/ml |
| Weight of Aqueous Phase | 1811.25 g |
| Volumetric Ratio, Aqueous Phase/Organic Phase | 1.05 |
| Volume of Organic Phase | 1665.0 ml |
| Density of Organic Phase | 0.84093 g/ml |
| Weight of Organic Phase, Excluding Initiator Charge | 1400.15 g |
| Total Reaction Volume | 3415.0 ml |
| Total Reaction Weight | 3211.40 g |

TABLE 1B-continued

Material Charges for a Typical Five (5) Liter-Reactor Polymerization Run

| | |
|---|---|
| Initiator, Pure Benzoyl Peroxide (BPO) | 8.07606 g |
| Initiator, 97% BPO | 8.3258 g |
| (Note: Initiator charge is calculated on only the quantity of polymerizable monomers introduced into the reactor.) | |
| Commercial 63% Divinylbenzene (DVB) [98.65 Polymerizable Monomers of DVB and EVB (Ethylvinylbenzene); 1.35% inert compounds; 63.17% DVB; 35.48% EVB] | 794.814 g |
| Toluene | 269.300 g |
| Isooctane | 336.036 g |
| Benzoyl Peroxide, 97% | 8.3258 g |
| Total, Organic Charge | 1408.4758 g |

Upon preparation of the aqueous phase and the organic phase, the aqueous phase is poured into the five-liter reactor and heated to 65° C. with agitation. The pre-mixed organic phase including the initiator is poured into the reactor onto the aqueous phase with the stirring speed set at the rpm for formation of the appropriate droplet size. The dispersion of organic droplets is heated to the temperature selected for the polymerization and is held at this temperature for the desired length of time to complete the conversion of the monomers into the crosslinked polymer and, thereby, set the pore structure. Unreacted initiator is destroyed by heating the bead slurry for two (2) hours at a temperature where the initiator half-life is one hour or less. For the initiator, benzoyl peroxide, the unreacted initiator is destroyed by heating the slurry at 95° C. for two (2) hours.

The slurry is cooled, the mother liquor is siphoned from the beads and the beads are washed five (5) times with ultrapure water. The beads are freed of porogen and other organic compounds by a thermal cleaning technique. This process results in a clean, dry porous adsorbent in the form of spherical, porous polymer beads.

TABLE 1C

Components of Adsorbent Syntheses

| Porous Polymer Identity | Adsorbent 1 Wt. %[a] | Adsorbent 2 | Adsorbent 3 Wt. %[a] | Adsorbent 4 Wt. %[a] | Adsorbent 5 Wt. %[a] |
|---|---|---|---|---|---|
| Divinylbenzene, (DVB), Pure | 35.859 | Adsorbent 2 is a comercial resin, Amberlite XAD-16 ®, made by Rohm and Haas Company | 26.163 | 22.4127 | 22.4127 |
| Ethylvinylbenzene (EVB), Pure | 20.141 | | 14.695 | 12.5883 | 12.5883 |
| Inerts | 0.766 | | 0.559 | 0.4790 | 0.4790 |
| Toluene | 19.234 | | 27.263 | 64.521 | 54.841 |
| Isooctane | 24.00 | | 31.319 | 0.00 | 9.680 |
| Polymerizable Monomers | 56.00 | | 40.8584 | 35.00 | 35.00 |
| Porogen | 44.00 | | 59.1416 | 65.00 | 65.00 |
| Benzoyl Peroxide (BPO), Pure; Wt. % Based Upon Polymerizable Monomer Content | 1.03 | | 0.7447 | 2.00 | 4.00 |
| Polymerization, ° C./time, hrs. | 75°/10 hrs | | 80°/16 hrs | 70°/24 hrs 95°/2 hrs | 65°/24 hrs 95°/2 hrs |

[a]Wt. % value is based upon the total weight of the organic phase excluding the initiator.

EXAMPLE 2

Pore Structure Characterization

The pore structures of the adsorbent polymer beds identified in TABLE 1C were analyzed with a Micromeritics ASAP 2010 instrument. The results are provided in GRAPH 1 where the pore volume is plotted as a function of the pore diameter. This graph displays the pore volume distribution across the range of pore sizes.

The pore volume is divided up into categories within pore size ranges for each of the five adsorbent polymers and these values are provided in TABLE 2. The Capacity Pore Volume is that pore volume that is accessible to protein sorption and consists of the pore volume in pores larger than 100 Å diameter. The Effective Pore Volume is that pore volume that is selectively accessible to proteins smaller than 35,000 Daltons and consists of pore diameters within the range of 100 to 250 Å diameter. The Oversized Pore Volume is the pore volume accessible to proteins larger than 35,000 Daltons and consists of the pore volume in pores larger than 250 Å diameter. The Undersize Pore Volume is the pore volume in pores smaller than 100 Å diameter and is not accessible to proteins larger than about 10,000 Daltons.

TABLE 2

Pore Structure Characterization of Adsorbents

| Porous Polymer Identity | Adsorbent 1 | Adsorbent 2 | Adsorbent 3 | Adsorbent 4 | Adsorbent 5 |
|---|---|---|---|---|---|
| Capacity Pore Volume, cc/g; Dp, 100 Å → 2000 Å | 0.5850 | 1.245 | 1.5156 | 0.3148 | 0.6854 |
| Effective Pore Volume, cc/g; Dp, 100 Å → 250 Å | 0.5678 | 0.986 | 0.3330 | 0.3060 | 0.6728 |
| Oversized Pore Volume, cc/g; Dp >250 Å | 0.0172 | 0.259 | 1.1826 | 0.0089 | 0.0126 |
| Undersized Pore Volume, cc/g; Dp <100 Å | 0.3941 | 0.534 | 0.4068 | 0.6311 | 0.4716 |
| Total Pore Volume, cc/g; Dp, 17 Å → 2000 Å | 0.9792 | 1.779 | 1.9225 | 0.9459 | 1.1569 |
| Effective Pore Volume In % of Capacity Pore Volume | 97.06 | 79.20 | 21.97 | 97.19 | 98.16 |

Note:
Dp is an acronym for diameter of pore.

FIG. 1 depicts a Graph of Table 2 showing a plot of pore volume v pore diameter (dV/dD vs. D) for Various Adsorbents Measured by Nitrogen Desorption Isotherm.

EXAMPLE 3

Protein Adsorption Selectivity

The polymeric adsorbent beads produced in Example 1 are wetted out with an aqueous solution of 20 wt. % isopropyl alcohol and thoroughly washed with ultrapure water. The beads with diameters within 300 to 850 microns are packed into a 200 ml hemoperfusion device which is a cylindrical cartridge 5.4 cm in inside diameter and 8.7 cm in length. The beads are retained within the cartridge by screens at each end with an orifice size of 200 microns. End caps with a center luer port are threaded onto each end to secure the screens and to provide for fluid distribution and attachment for tubing.

Four liters of an aqueous 0.9% saline solution buffered to a pH of 7.4 are prepared with 50 mg/liter of horse heart cytochrome-c and 30 g/liter of serum albumin. These concentrations are chosen to simulate a clinical treatment of a typical renal patient where albumin is abundant and $\beta_2$-microglobulin is at much lower levels in their blood. Horse heart cytochrome-c with a molecular weight 11,685 daltons has a molecular size very close to $\beta_2$-microglobulin at 11,845 daltons and, therefore, is chosen as the surrogate for $\beta_2$-microglobulin. Serum albumin is a much larger molecule than cytochrome-c with a molecular weight of 66,462 daltons and, therefore, allows for the appropriate competitive adsorption studies needed for selecting the porous polymer with the optimum pore structure for size-selective exclusion of albumin.

The protein solution is circulated by a dialysis pump from a reservoir through a flow-through UV spectrophotometer cell, the bead bed, and returned to the reservoir. The pumping rate is 400 ml/minute for a duration of four (4) hours. The concentration of both proteins in the reservoir is measured periodically by their UV adsorbance at 408 nm for cytochrome-c and at 279 nm for albumin.

All five adsorbents identified in TABLE 1C were examined by this competitive protein sorption assessment and the measured results are given in TABLE 3.

TABLE 3

Size-Selective Efficacy of Porous Polymeric Adsorbents

| Porous Polymer Identity | Adsorbent 1 | Adsorbent 2 | Adsorbent 3 | Adsorbent 4 | Adsorbent 5 |
|---|---|---|---|---|---|
| Capacity Pore Volume, cc/g; Dp, 100 Å → 2000 Å | 0.5850 | 1.245 | 1.5156 | 0.3148 | 0.6854 |
| Effective Pore Volume, cc/g; Dp, 100 Å → 250 Å | 0.5678 | 0.986 | 0.3330 | 0.3060 | 0.6728 |
| Effective Pore Volume In % of Capacity Pore Volume | 97.06 | 79.20 | 21.97 | 97.19 | 98.16 |
| % Cytochrome-C Adsorbed | 89.0 | 96.7 | 95.3 | 57.4 | 90.1 |
| % Albumin Adsorbed | 3.7 | 8.1 | 13.1 | 1.0 | 1.8 |
| Selectivity | 24.05 | 11.94 | 7.27 | 57.1 | 50.06 |

Note:
Selectivity = % Cytochrome-c Adsorbed/% Albumin Adsorbed

EXAMPLE 4

Pore Volume and Pore Size Range for Suitable Kinetics and Size-Selectivity for Cytochrome-C Over Albumin TABLE 3 and GRAPH 1 summarize the pertinent pore structure data and the protein perfusion results carried out on all five (5) adsorbents. The selectivity for adsorbing cytochrome-c over albumin decreased in the following order: Adsorbent 4>Adsorbent 5>Adsorbent 1>Adsorbent 2>Adsorbent 3.

The quantity of cytochrome-c adsorbed during the four hour perfusion decreased in the following order: Adsorbent 2>Adsorbent 3>Adsorbent 5>Adsorbent 1>Adsorbent 4.

Adsorbent 4 with the highest selectivity at 57.1 had the poorest kinetics picking up only 57.4% of the available cytochrome-c over the four hour perfusion. This kinetic result occurs from the Effective Pore Volume being located at the small end of the pore size range, having all its Effective Pore Volume within the pore size range of 130 to 100 Å. There is insignificant pore volume in pores larger than 130 Å and this small pore size retards the ingress of cytochrome-c.

Adsorbent 5 with its major pore volume between 100 to 200 Å had the second highest selectivity for cytochrome-c over albumin at 50.6 and it had good mass transport into the Effective Pore Volume pores picking up 90.1% of the cytochrome-c during the four hour perfusion. This porous polymer has the best balance of properties with excellent size-selectivity for cytochrome-c over albumin and very good capacity for cytochrome-c during a four hour perfusion.

Adsorbent 1 showed reasonably good selectivity at 24.05 for sorbing cytochrome-c over albumin. It also exhibited good capacity for sorbing cytochrome-c during the four hour perfusion, picking up 89.0% of the quantity available.

Adsorbent 2 with the highest capacity for sorbing cytochrome-c during the four hour perfusion picked up 96.7% of the available cytochrome-c. This high capacity arises from having a large pore volume, 0.986 cc/g, and within the Effective Pore Volume range of 100 Å to 250 Å. However, this porous polymer allowed more albumin to be adsorbed than Adsorbents 1, 4, and 5, since it has significant pore volume, 0.250 cc/g, in the pore size group from 250 Å to 300 Å.

Adsorbent 3 with a very broad pore size distribution (see GRAPH 1) had the poorest selectivity among the group at 7.27. It has a very large pore volume in the pore size range larger than 250 Å. This porous polymer has a pore volume of 1.15 cc/g within the pore size range of 250 Å to 740 Å. In contrast with the other four adsorbents, this porous polymer is not size-selective for proteins smaller than about 150,000 Daltons, although it did sorb 95.3% of the available cytochrome-c during the perfusion.

On balance of properties of selectively for sorbing cytochrome-c over albumin and its capacity for picking up cytochrome-c during a four hour perfusion, porous polymeric Adsorbent 5, gave the best performance. This porous polymer has the proper pore structure to perform well in hemoperfusion in concert with hemodialysis for people with End Stage Renal Disease.

Numerous modifications and variations of the present invention are possible in light of the above teachings. It is therefore to be understood that within the scope of the attendant claims attached hereto, this invention may be practiced other than as specifically disclosed herein.

What is claimed is:

1. A size-selective porous polymer comprising of a plurality of pores, wherein all of said pores of said polymer have diameters from greater than 100 Angstrom to about 300 Angstrom, said polymer being capable of sorbing protein molecules greater than 20,000 to less than 50,000 Daltons from blood and excluding the sorption of blood proteins greater than 50,000 Daltons, said polymer having an effective pore volume and a capacity pore volume, said effective pore volume is from at least 0.306 cc/g to 0.986 cc/g, said effective pore volume is from at least 21.97% to 98.16% of said polymer's capacity pore volume, said effective pores having diameters from greater than 100 Angstroms to about 250 Angstroms and said polymer having oversized pores with a diameter greater than 251 Angstroms.

2. The polymer of claim 1 wherein said polymer is biocompatible.

3. The polymer of claim 1 wherein said polymer is hemocompatible.

4. The polymer of claim 1 wherein the geometry of said polymer is a spherical bead.

5. The polymer of claim 1 wherein said polymer is used in direct contact with whole blood to sorb protein molecules selected from a group consisting essentially of cytokines and $\beta_2$-microglobulin and exclude the sorption of large blood proteins, said large blood proteins being selected from a group consisting essentially of hemoglobin, albumin, immunoglobulins, fibrinogen, serum proteins and other blood proteins larger than 50,000 Daltons.

6. The polymer of claim 1 wherein said polymer has an internal surface selectivity for adsorbing proteins smaller than 50,000 Daltons, having little to no selectivity for adsorbing vitamins, glucose, electrolytes, fats, and other hydrophilic small molecular nutrients carried by the blood.

7. The polymer of claim 1 wherein said polymer is made using suspension polymerization.

8. The polymer of claim 1 wherein said polymer is constructed from aromatic monomers of styrene and ethylvinylbenzene with a crosslinking agent selected from a group consisting essentially of divinylbenzene, trivinylcyclohexane, trivinylbenzene, divinylnaphthalene, divinylsulfone, trimethylolpropane triacrylate, trimethylolpropane trimethacrylate and mixtures thereof.

9. The polymer in claim 8 wherein a stabilizing agent for the droplet suspension polymerization is selected from a group consisting essentially of hemocompatibilizing polymers, said polymers being poly(N-vinylpyrrolidinone), poly(hydroxyethyl acrylate), poly(hydroxyethyl methacrylate), hydroxylethyl cellulose, hydroxypropyl cellulose, salts of poly(acrylic acid), salts of poly(methacrylic acid), poly(dimethylaminoethyl acrylate), poly(dimethylaminoethyl methacrylate), poly(diethylaminoethyl acrylate), poly(diethylaminoethyl methacrylate), poly(vinyl alcohol) and mixtures thereof.

10. The polymer of claim 1 wherein said polymer is made hemocompatible by exterior coatings selected from a group consisting essentially of poly(N-vinylpyrrolidinone), poly(hydroxyethyl acrylate), poly(hydroxyethyl methacrylate), hydroxyethyl cellulose, hydroxypropyl cellulose, salts of poy(acrylic acid), salts of poly(methacrylic acid), poly(dimethylaminoethyl methacrylate), poly(dimethylaminoethyl acrylate), poly(diethylaminoethyl acrylate), poly(diethylaminoethyl methacrylate), poly(vinyl alcohol) and mixtures thereof.

11. The polymer of claim 10 wherein said polymer is made hemocompatible by surface grafting of the hemocompatible exterior coatings concomitantly with formation of the porous polymer beads.

12. The polymer of claim 10 wherein said polymer is made hemocompatible by surface grafting of the hemocompatible exterior coatings onto the preformed porous polymeric beads.

13. A size selective polymer comprising of a plurality of pores wherein all of said pores have diameters from greater than 100 Angstrom to about 300 Angstrom, said polymer designed to sorb cytokines and $\beta_2$-microglobulin and exclude the sorption of large blood borne proteins, said large blood borne proteins being selected from a group consisting essentially of hemoglobin, albumin, immunoglobulins, fibrinogen, serum proteins and other blood proteins larger than 50,000 Daltons, said polymer having an effective pore volume of at least 0.306 cc/g to 0.986 cc/g, said effective pores having diameters from greater than 100 Angstroms to about 250

Angstroms and said polymer having oversized pores with a diameter greater than 251 Angstroms.

14. The polymer of claim 13 wherein said polymer is made using suspension polymerization.

15. The polymer of claim 13 wherein said polymer is made porous using macroreticular synthesis.

16. The polymer of claim 13 wherein said polymer has an internal surface selectivity for adsorbing proteins smaller than 50,000 Daltons, having little to no selectivity for adsorbing vitamins, glucose, electrolytes, fats, and other hydrophilic small molecular nutrients carried by the blood.

17. A polymer comprising of a plurality of pores, wherein all of said pores of said polymer have diameters from greater than 75 Angstrom to about 300 Angstrom, said polymer being capable of sorbing protein molecules greater than 20,000 Daltons from blood and excluding the sorption of blood proteins greater than 50,000 Daltons, said polymer having an effective pore volume and a capacity pore volume, said effective pore volume is at least 21.97% to 98.16% of said polymer's capacity pore volume, said effective pores having diameters from greater than 100 Angstroms to about 250 Angstroms and said polymer having oversized pores with a diameter greater than 251 Angstroms.

* * * * *